United States Patent
Kim et al.

(10) Patent No.: US 9,968,413 B2
(45) Date of Patent: May 15, 2018

(54) SURGICAL OPERATION BY WIRE TYPE SURGICAL OPERATION APPARATUS

(71) Applicant: SEOUL NATIONAL UNIVERSITY R&DB FOUNDATION, Seoul (KR)

(72) Inventors: Sungwan Kim, Seoul (KR); Youdan Kim, Seoul (KR); Hyeon Hoe Kim, Seoul (KR); Hee Chan Kim, Seoul (KR); Yong Hyun Park, Seoul (KR); Chiwon Lee, Gyeonggi-Do (KR); Wonshik Kim, Chungcheongnam-do (KR); Chiyul Yoon, Seoul (KR); Seungwoo Noh, Busan (KR); Choonghee Lee, Seoul (KR)

(73) Assignee: Seoul National University R&DB Foundation, Seoul (KR)

(*) Notice: Subject to any disclaimer, the term of this patent is extended or adjusted under 35 U.S.C. 154(b) by 112 days.

(21) Appl. No.: 15/012,700

(22) Filed: Feb. 1, 2016

(65) Prior Publication Data

US 2016/0143701 A1    May 26, 2016

Related U.S. Application Data

(62) Division of application No. 14/078,395, filed on Nov. 12, 2013, now abandoned.

(30) Foreign Application Priority Data

Feb. 26, 2013  (KR) .................. 10-2013-0020382
Nov. 6, 2013   (KR) .................. 10-2013-0134162

(51) Int. Cl.
*A61B 17/00*  (2006.01)
*A61B 34/37*  (2016.01)
(Continued)

(52) U.S. Cl.
CPC .............. *A61B 34/37* (2016.02); *A61B 34/30* (2016.02); *A61B 2017/00402* (2013.01); *A61B 2017/2927* (2013.01); *A61B 2034/305* (2016.02)

(58) Field of Classification Search
CPC ........ A61B 17/00234; A61B 17/22031; A61B 17/28; A61B 17/282; A61B 17/29;
(Continued)

(56) References Cited

U.S. PATENT DOCUMENTS

2007/0288044 A1* 12/2007 Jinno ............... A61B 17/29
                                                     606/174
2010/0016852 A1*  1/2010 Manzo .............. A61B 34/71
                                                     606/46
2012/0116391 A1   5/2012 Houser et al.

FOREIGN PATENT DOCUMENTS

JP      05-168584       7/1993
KR   10-2012-0120837   11/2012

* cited by examiner

*Primary Examiner* — Melanie Tyson
(74) *Attorney, Agent, or Firm* — Wells St. John P.S.

(57) ABSTRACT

Disclosed herein is a surgical operation by wire (SOBW) type surgical operation apparatus including an end effector configured so as to remove or minimize configurations of a mechanical cable. The SOBW type surgical operation apparatus includes: a body part; an extension part having one end connected to the body part; and an end effector formed at the other end of the extension part, and receiving electrical energy transferred through the body part and the extension part and converting the electrical energy into mechanical energy.

6 Claims, 9 Drawing Sheets

(51) Int. Cl.
*A61B 34/30* (2016.01)
*A61B 17/29* (2006.01)

(58) Field of Classification Search
CPC .......... A61B 2017/00017; A61B 2017/00402;
A61B 2017/2903; A61B 2017/2926;
A61B 2017/2927; A61B 2017/2947;
A61B 19/22; A61B 19/2203
USPC .................................................. 606/205–208
See application file for complete search history.

SURGICAL OPERATION BY WIRE TYPE SURGICAL OPERATION APPARATUS

CROSS REFERENCE TO RELATED APPLICATIONS

This application resulted from a division of U.S. patent application Serial No. 14/078,395, which was filed Nov. 12, 2013, which claims priority to Korean Patent Application No. 10-2013-0020382, filed on Feb. 26, 2013, and Korean Patent Application No. 10-2013-0134162, filed on Nov. 6, 2013, all of which are hereby incorporated herein by reference.

BACKGROUND OF THE INVENTION

1. Technical Field

The present invention relates to a surgical operation by wire (SOBW) type surgical operation apparatus. More specifically, the present invention relates to an SOBW type surgical operation apparatus including an end effector configured so as to remove or minimize configurations of a mechanical cable.

2. Description of the Related Art

A surgical operation apparatus such as a surgical operation robot inserts a small surgical operation tool into a human body in which a surgical operation area is positioned to perform minimally invasive surgery. The surgical operation apparatus includes extension parts connected to a body part thereof, such as a plurality of robot arms, and the like. The extension part may include a passive part and an active part, wherein the passive part is a part that may be manually effected by a preparation step before a surgical operation and the active part is a part effected according to an action of a worker such as a doctor, or the like, at the time of performing the surgical operation.

The active part is mounted with a surgical operation tool inserted into the abdominal cavity, a joint, or the like, in the human body to perform a surgical operation work such as photographing, resection, or the like. The surgical operation tool is called an end effector in the surgical operation robot and generally may perform motion in five directions such as vertical motion, horizontal motion, forward and reverse motion, rotational motion, and forceps motion. In addition, a mechanical cable extension part such as a robot arm, or the like, may be provided with one or more joint part in order to effectively access the affected part.

In the surgical operation apparatus according to the related art, the end effector and/or the joint part are driven by a cable extended from the body part to the active part, and the body part or the passive part of the surgical operation apparatus such as the surgical operation robot, or the like, is provided with a driver for driving the cable. Korean Patent Application Publication No. 10-2012-0120837 entitled "Apparatus for Measuring Force of Robot Arm Operating Cable Using Optical Fiber Bragg Grating Sensor and Remote Robot Arm Operating Apparatus Using the Same" has disclosed a configuration using an optical fiber Bragg grating sensor in order to measure force of a cable. However, in the case of driving the end effectors and/or the joint parts of the surgical operation apparatus using the cables, when the number of joint parts is increased or a length of the extension part such as the robot arm, or the like, is increased, the number of cables or lengths of the cables are also increased in proportion to the number of joint parts or the length of the extension part, such that a mechanical connection structure with the surgical operation apparatus provided with the driver for driving the cable may be complicated.

This causes a similar problem also in the case in which a degree of freedom of motion of the end effector is increased. In addition, this increases a size of the surgical operation apparatus provided with the driver.

That is, motion of the cable for driving a distal end joint in the surgical operation apparatus including a plurality of joints may have an influence on motion of other joints, and backlash may be increased as a distance between the driver and the joint part and/or the end effector of the surgical operation apparatus becomes distant. Large tension is applied to the cable in order to decrease the backlash. As a result, a problem that the cable is cut or deformed during a surgical operation may occur.

SUMMARY OF THE INVENTION

An object of the present invention is to prevent a mechanical cable from being extended and cut and prevent a backlash phenomenon by minimizing configurations of the mechanical cable.

Another object of the present invention is to improve work precision of an end effector.

In an aspect, the present invention provides a surgical operation by wire (SOBW) type surgical operation apparatus, including: a body part; an extension part having one end connected to the body part; and an end effector formed at the other end of the extension part, and receiving electrical energy transferred through the body part and the extension part and converting the electrical energy into mechanical energy.

In another aspect, the present invention provides an SOBW type surgical operation apparatus, including: a body part; an extension part having one end connected to the body part; and an end effector formed at the other end of the extension part, receiving electrical energy transferred through the body part and the extension part, and performing a gripping operation, a pitching operation, and a yawing operation using the electrical energy.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Preferred embodiments of the present invention will be described in detail with reference to the accompanying drawings. In the present specification, an overlapped description and a detailed description for well-known functions and configurations that may obscure the gist of the present invention will he omitted. Preferred embodiments of the present invention are provided in order to more completely explain the present invention to those skilled in the art. Therefore, throughout the accompanying drawings, shapes, sizes, and the like, of components may be exaggerated for clarity.

Hereinafter, configurations and operations of a surgical operation by wire (SOBW) type surgical operation apparatus according to a preferred embodiment of the present invention will he described.

Figure 1:
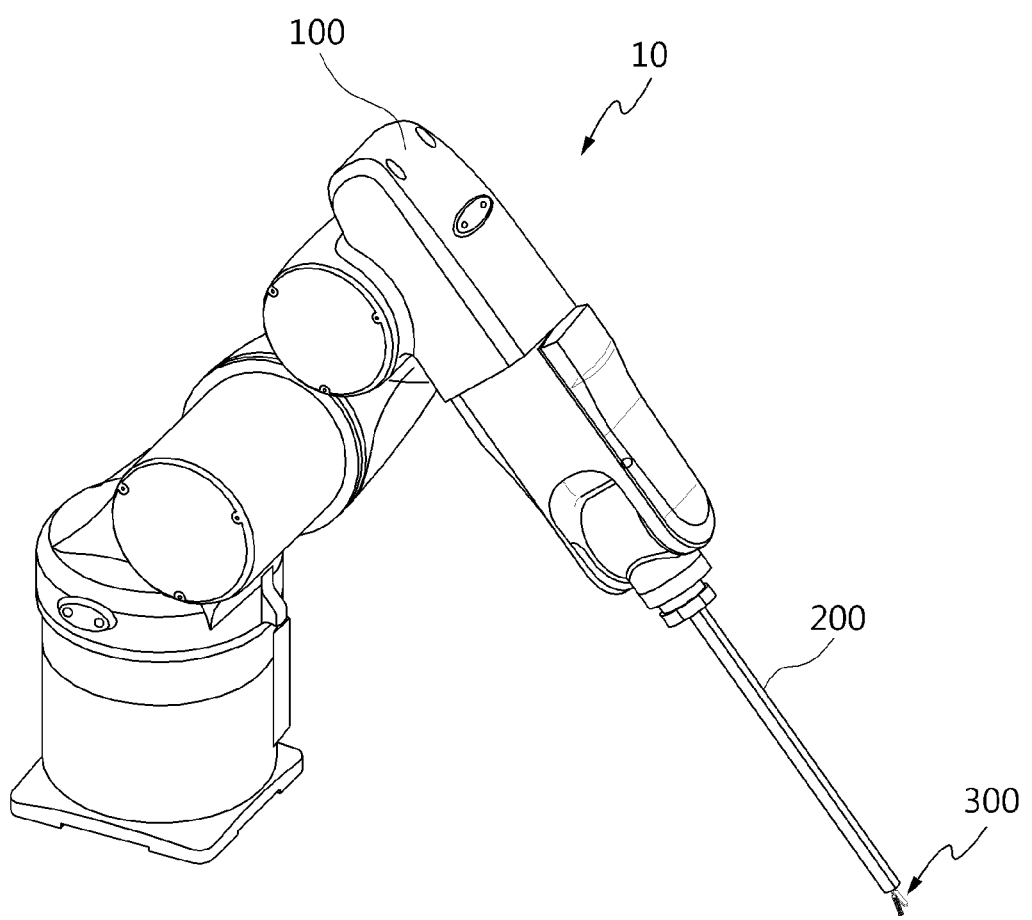
FIG. 1 is a perspective view illustrating a surgical operation by wire (SOBW) type surgical operation apparatus according to a preferred embodiment of the present invention.
Figure 2:
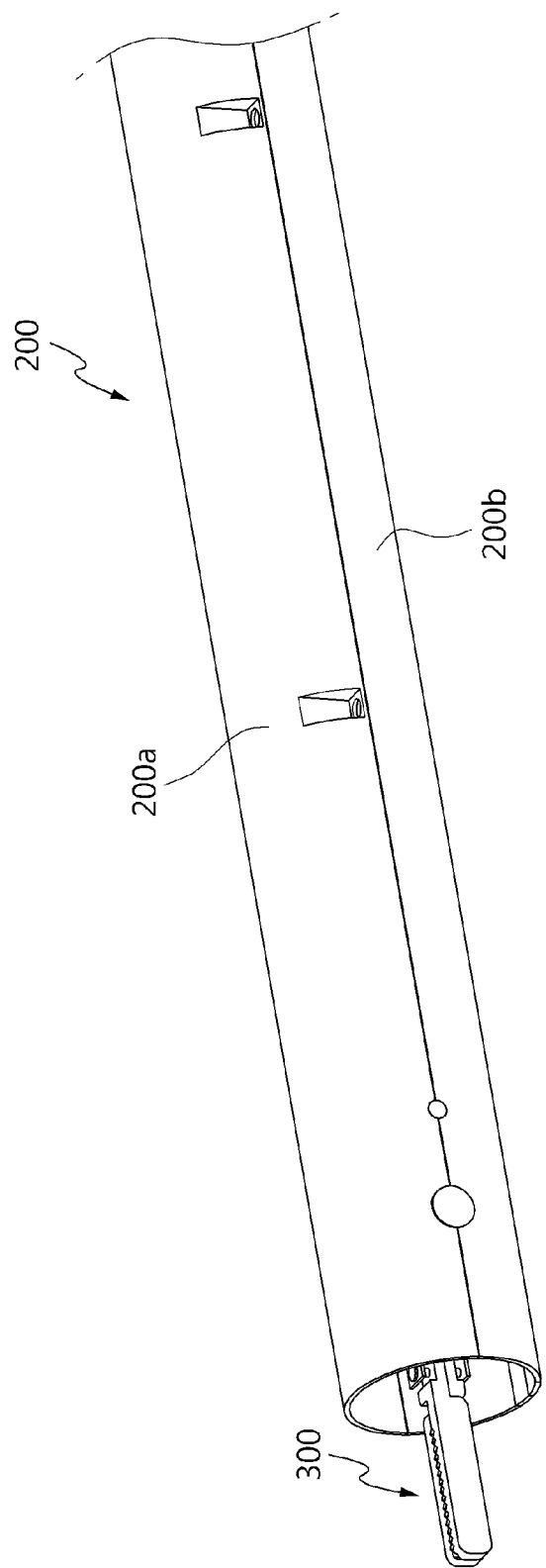
FIG. 2 is an enlarged perspective view of configurations of an extension part and an end effector according to the preferred embodiment of the present invention.

FIG. 1 is a perspective view illustrating a surgical operation by wire (SOBW) type surgical operation apparatus according to a preferred embodiment of the present invention. FIG. 2 is an enlarged perspective view of configurations of an extension part and an end effector according to the preferred embodiment of the present invention.

Referring to FIG. 1, the SOBW type surgical operation apparatus 10 according to the preferred embodiment of the present invention is configured to include a body part 100, an extension part 200, and an end effector 300.

The body part 100 is supported by a around, a wall, a ceiling, or the like.

One end of the extension part 200 is connected to the body part 100. Referring FIGS. 1 and 2, the extension part 200 may include an upper cover part 200a and a lower cover part 200b.

The end effector 300 is formed at the other end of the extension part 200 and accesses a surgical operation target site to perform a surgical operation work. The end effector 300 may be inserted and positioned into inner portions of the upper and lower cover parts 200a and 200b at the other end of the extension part 200.

The end effector 300 receives electrical energy transferred through the body part 100 and the extension part 200 and converts the electrical energy into mechanical energy for the surgical operation work. More specifically, the end effector 300 performs a gripping operation, a pitching operation, and a yawing operation using the electrical energy. Here, the extension part 200 includes an electrical wire (hereinafter, referred to as a "wire") extended from the body part 100 and transfers the electrical energy to the end effector 300 through the wire (not illustrated). That is, a power source is positioned at the body part 100, and the electrical energy generated by the power source is transferred to the end effector 300 through the body part 100 and the extension part 200.

In the preferred embodiment of the present invention, a rolling operation of the end effector 300 is implemented by the body part 100 of FIG. 1, that is, a robot arm. The reason for this is to implement a structure for decreasing a size and a weight of an effector. That is, since the extension part 200 is rotated by the robot arm, the size and the weight of the end effector 300 may be decreased as compared with those of a structure in which a separate driving part is provided so as to be adjacent to an actuating part for rotating the end effector 300 disposed at a distal end of the extension part 200.

In addition, the rolling operation may also be implemented by additionally disposing a motor in the extension part.

Hereinafter, a configuration and a gripping operation of the end effector according to the preferred embodiment of the present invention will he described in more detail.

Figure 3:
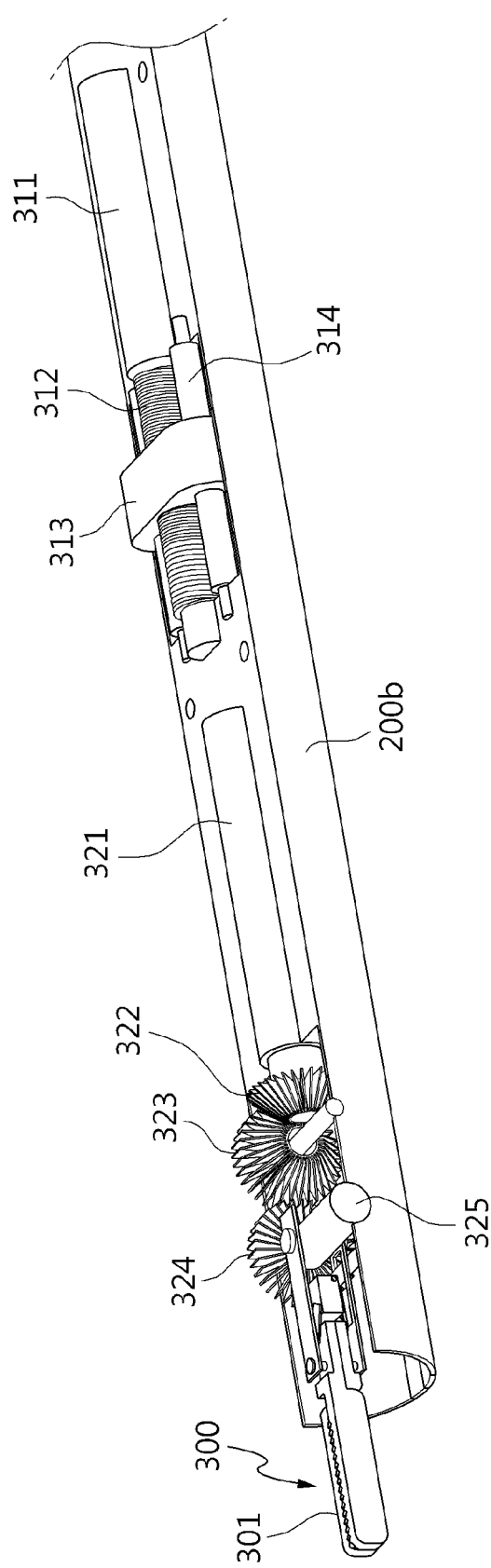
FIG. 3 is a perspective view illustrating a configuration in which an upper cover part is removed from the configuration of FIG. 2.
Figure 4:
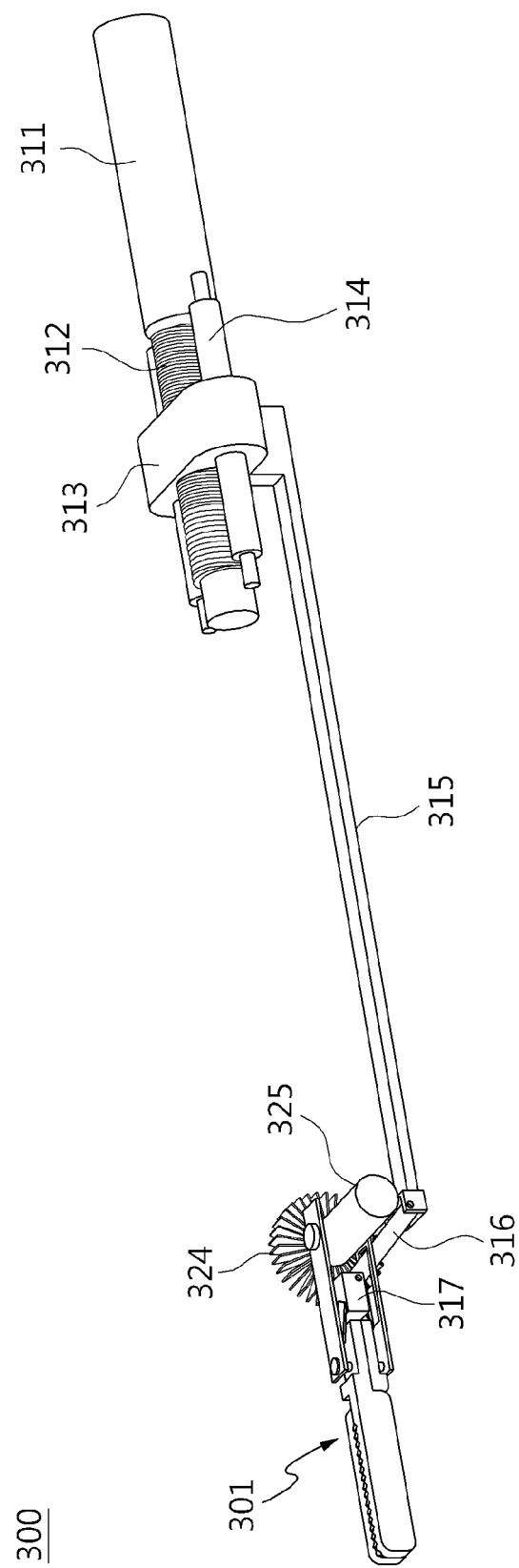
FIG. 4 is a perspective view illustrating the end effector after some configurations of a lower cover part and a pitching operator are removed from the configuration of FIG. 3.
Figure 5:
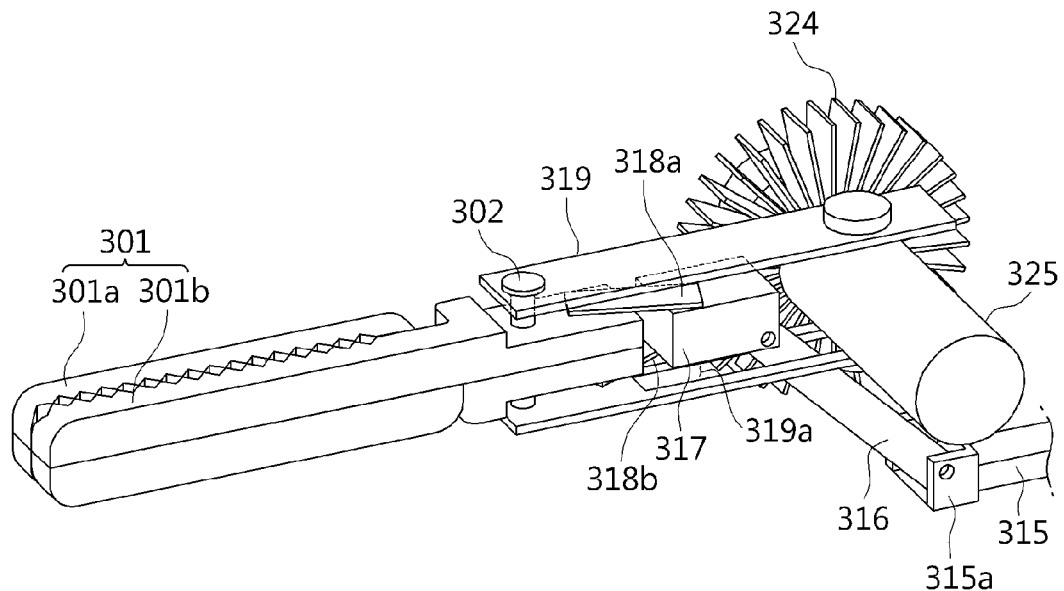
FIGS. 5 and 6 are views for describing a gripping operation of a forceps part.
Figure 6:
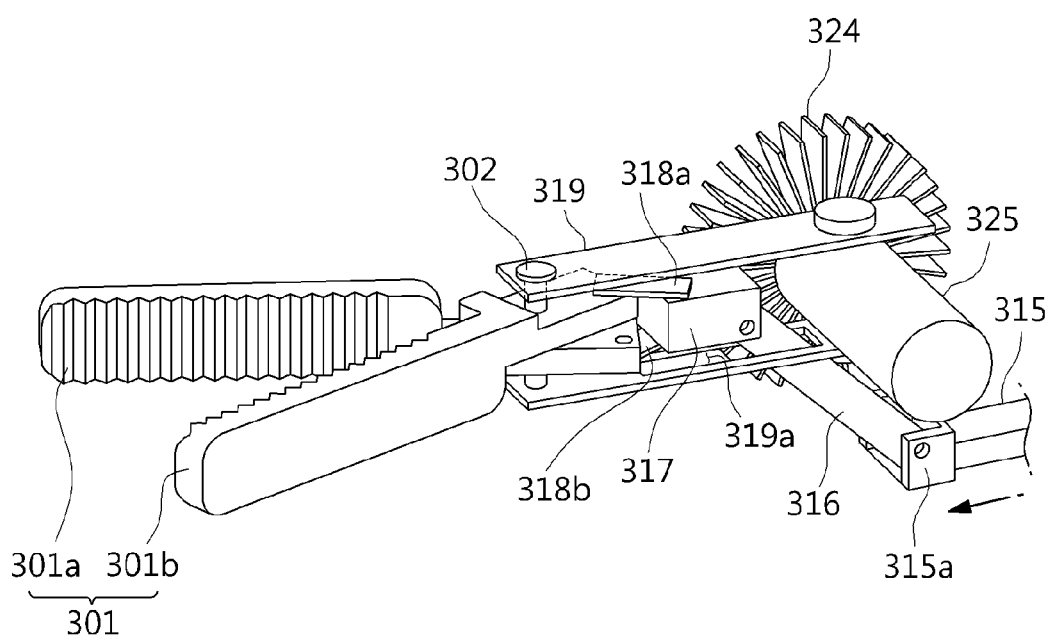

FIG. 3 is a perspective view illustrating a configuration in which an upper cover part is removed from the configuration of FIG. 2. FIG. 4 is a perspective view illustrating the end effector after some configurations of a lower cover part and a pitching operator are removed from the configuration of FIG. 3. FIGS. 5 and 6 are views for describing a gripping operation of a forceps part.

Referring to FIGS. 3 and 4, the end effector 300 according to the preferred embodiment of the present invention may be configured to include an effector 301, a gripping operator, and a pitching operator.

The effector 301 may he formed of forceps including first and second legs 301, a and 301b. The effector 301 may be supported to a support member 319 to be described below through a support pin 302. In addition, the first and second legs 301a and 301b may perform a gripping operation based on the support pin 302. The gripping operation of the first and second legs 301a and 302b will be described below in a description of FIGS. 5 and 6.

In addition, the effector 301 may be forceps, scissors, a needle driver, a clip applier, a probe grasper, or a retractor. The forceps, or the like, access the surgical operation target site to perform gripping, pitching, rolling, or yawing motion.

A spur gear is a cylindrical gear in which sterns of gear teeth are oriented parallel to an axis of the gear and is connected to another gear in such a way that two external gears engage with each other. The spur gear is used to transmit power when two axes are parallel to each other so that force generated from the motor may be precisely transmitted to the end effector that is a surgical operation tool. A rack gear refers to a rack on which gear teeth are linearly arranged in a shape wherein the number of teeth of a cylindrical gear that is a spur gear is infinitely increased such that the diameter of the cylinder becomes infinite. The rack gear may be used to convert rotational motion into linear motion or, on the contrary, it may be used to convert linear motion into rotational motion.

A helical gear is a gear which has teeth, the sterns of which are formed to have twisted curved surfaces, unlike the spur gear, to prevent the entire lengths of the stems of the gear teeth from engaging with each other at the same time. Compared to the spur gears, the helical gears more smoothly engage with each other so that vibration or noise may be reduced when the gears rotate. Further, since the length of a contact line of the helical gear is longer than that of the spur gear, the helical gear may be used to transmit more power.

Bevel gears engage with each other in such a way that two axes of the gears intersect at 90°. A worm gear is configured such that an axis thereof intersects, at a right angle, an axis of a gear that engages with the worm gear. In a manner similar to the bevel gears, the worm gear is used to transmit power in a perpendicular direction. Since the worm gear may make a comparatively high gear ratio, the size of a structure using the worm gear may be reduced to about half of the size of a structure using bevel gears or helical gears in the same conditions. Furthermore, the worm gear has an advantage of reduced noise or vibration compared to the other kinds of gears.

The gripping operator receives the electrical energy transferred from the body part and the extension part to induce a gripping operation of the effector 301. Hereinafter, a gripping operation of the gripping operator will be described under the assumption that the effector 301 is the forceps. However, the effector 301 may be various surgical operation apparatuses such as forceps, scissors, a needle driver, a clip applier, a probe grasper, a retractor, or the like. Therefore, in the present specification, the gripping operation is used as a term encompassing a surgical operation work of the surgical operation apparatuses.

The gripping operator may be configured to include a gripping motor part 311, a screw member 312, a female screw member 313, a screw guide 314, a gripping extension part 315, a sub extension part 316, a linear motion transfer member 317, a first connection member 318a, a second connection member 318b, and a support member 319.

The gripping motor part 311 converts the electrical energy transferred through the body part 100 and the extension part 200 into rotational motion.

The screw member 312 is formed at one side of the gripping motor part 311 and is rotated according to rotation of the gripping motor part 311. In addition, the screw member 312 has a screw thread formed on a surface thereof.

The female screw member 313 is coupled to an outer portion of the screw member 312 so as to enclose the screw member 312. In addition, the female screw member 313 may have a screw thread formed on an inner surface thereof contacting the screw member 312 and corresponding to the screw thread of the screw member 312. Therefore, the female screw member 313 linearly moves along the screw guide 314 according to the rotation of the screw member 312.

The gripping extension part 315 has one end coupled to one side of the female screw member 313. Therefore, the gripping extension part 315 linearly moves together with the female screw member 313 according to the linear motion of the female screw member 313. All of the female screw member 313, the screw guide 314, and the gripping extension part 315 may be called a gripping extension part.

The sub extension part 316 is extended from the other end of the gripping extension part 315. In addition, the sub extension part 316 is pivot-coupled to the other end of the gripping extension part 315 through a pivot coupling part 315a and is extended from the other end of the gripping extension part 315 toward the effector 301.

The linear motion transfer member 317 is formed at an end of the sub extension part 316. In addition, the linear motion transfer member 317 may convert mechanical kinetic energy transferred through the female screw member 313, the screw guide 314, the gripping extension part 315, and the sub extension part 316 into linear motion for the effector 301. Here, the linear motion transfer member 317 may have the first connection member 318a and the second connection member 318b formed at one side and the other side thereof, respectively, wherein the first and second connection members 318a and 318b may transfer force to one ends of the first and second legs 301a and 301b in different directions, respectively.

The support member 319 may be formed to support the effector 301 through a support pin 302. In addition, the support member 319 may have a groove part 319a formed in a portion of an inner side thereof to accommodate motion of the sub extension part 316 inward.

Referring to FIGS. 5 and 6 in more detail with respect to the gripping operation of the effector 301, the female screw member 313 and the gripping extension part 315 linearly move by the rotation of the gripping motor part 311 and the screw member 312. In addition, the sub extension part 316 allows the liner motion transfer member 317 to linearly move according to the linear motion of the gripping extension pan 315. Therefore, the first and second connection members 318a and 318b transfer force to one ends of the first and second legs 301a and 301b in different directions, respectively. As a result, the effector 301 performs the gripping operation.

The pitching operator receives the electrical energy transferred from the body part and the extension part to induce a pitching operation of the effector 301. A configuration and an operation of the pitching operator will be described in detail, together with a third gear 324 and a third gear support bar 325 that are not described, with reference to FIGS. 7 to 9.

Hereinafter, configurations and operations of an end effector used in an SOBW type surgical operation apparatus according to another preferred embodiment of the present invention will be described.

Figure 7:
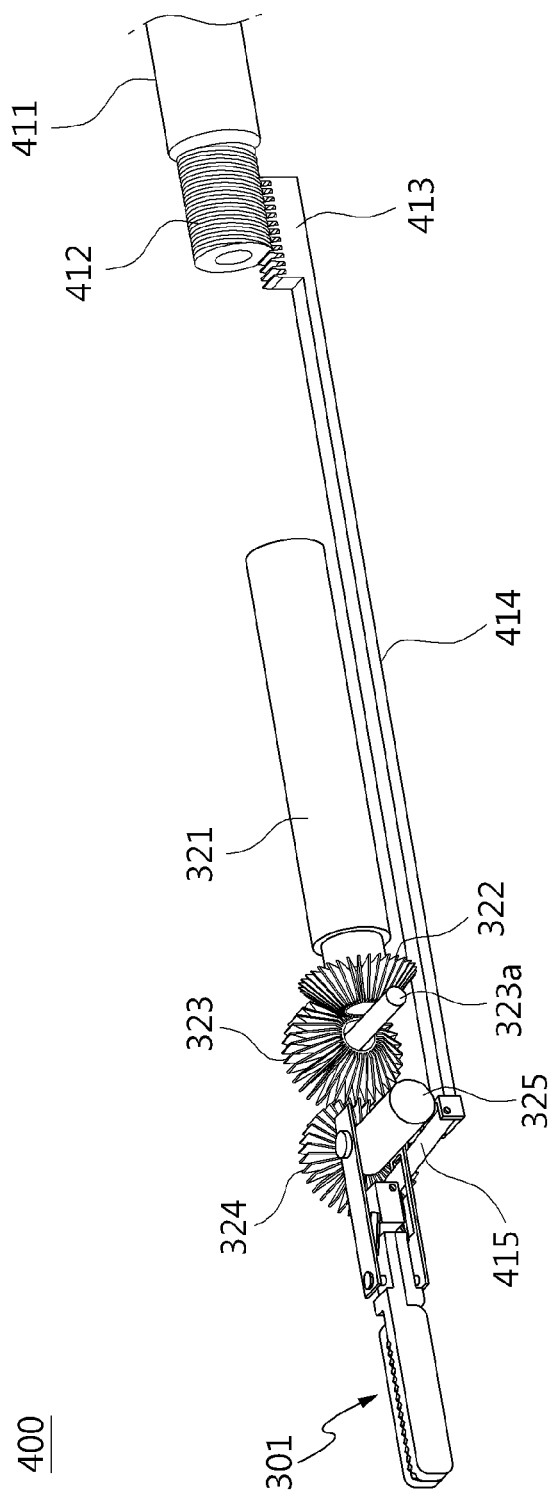
FIG. 7 is a perspective view illustrating an end effector according to another preferred embodiment of the present invention.
Figure 8:
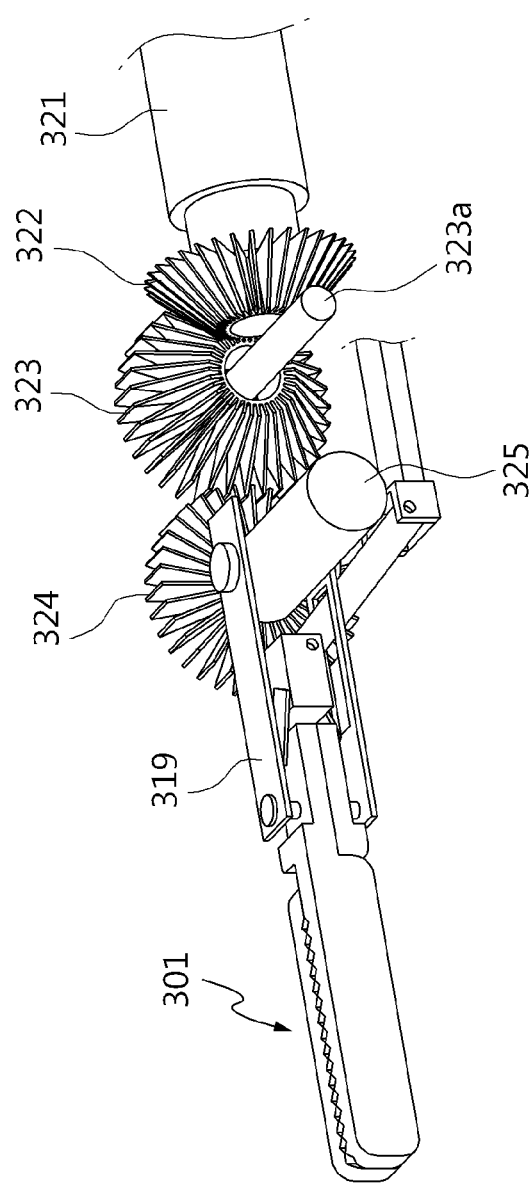
FIGS. 8 and 9 are views for describing a pitching operation of the forceps part.
Figure 9:
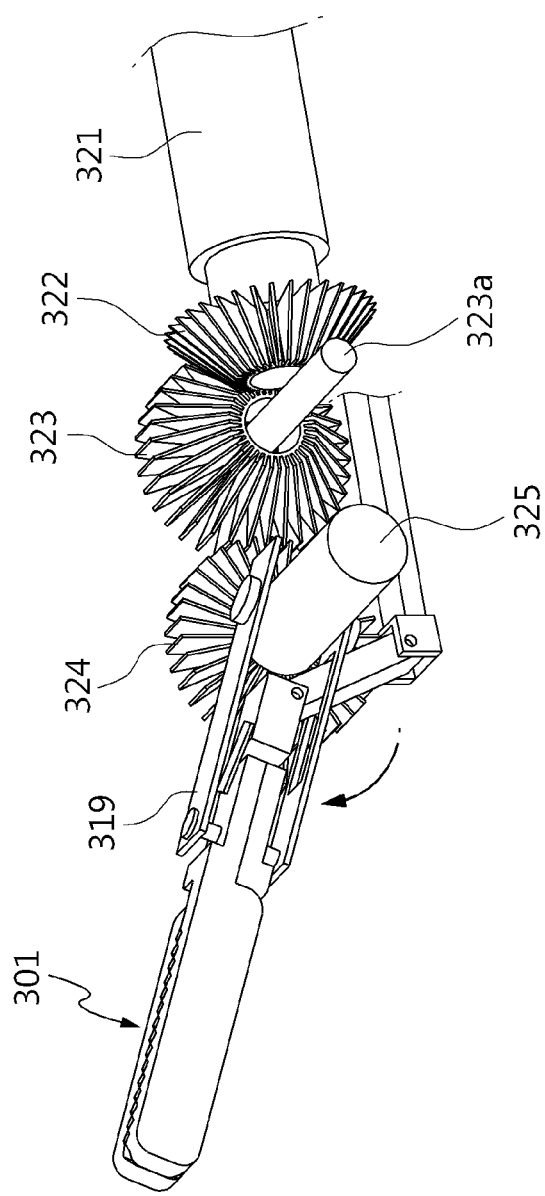

FIG. 7 is a perspective view illustrating an end effector according to another preferred embodiment of the present invention. FIGS. 8 and 9 arc views for describing a pitching operation of the forceps part.

The end effector 400 according to another preferred embodiment of the present invention is different from the end effector 300 illustrated in FIGS. 3 and 4 in view of a configuration of a gripping operator, but is the same as the end effector 300 illustrated in FIGS. 3 and 4 in view of a configuration of the pitching operator. Hereinafter, configurations similar to those of the end effectors 300 illustrated in FIGS. 3 and 4 will be denoted by the same terms and a detailed description thereof will be omitted.

In the end effector 400 according to another preferred embodiment of the present invention, the gripping operator may be configured to include a gripping motor part 411, a screw member 412, a counter screw member 413, a gripping extension part 414, and a sub extension part 415. Here, the counter screw member 413 may be formed to contact only a surface of one side of the screw member 412. The counter screw member 413 converts rotational motion of the gripping motor part 411 and the screw member 412 into linear motion.

Additionally, the gripping motor part 411 of the gripping operator may be formed of a linear motor. Since the linear motor directly generates linear driving force unlike a general rotation type motor, the linear motor may be used more effectively than the rotating motor, in a system requiring linear driving force. The reason is that in the case of generating linear driving force by a rotation type motor in a linear driving system, mechanical conversion devices such as a screw, a chain, a gear, and the like, are required, which causes energy loss and generation of noise due to friction.

In addition, the pitching operator may be configured to include a pitching motor part 321 and a gear part including a first gear 322, a second gear 323, and a third gear 324.

The pitching motor part 321 converts the electrical energy transferred through the body part and the extension part into rotational motion.

Referring to FIGS. 8 and 9 in more detail with respect to the pitching operation of the effector 301, the first gear 322 of the gear part accommodates rotational motion of the pitching motor part 321, such that it rotates, in addition, the second gear 323 formed perpendicularly to the first gear 322 and supported to a second gear support bar 323a and the third gear 324 formed perpendicularly to the first gear 322 and supported to a third gear support bar 325 engage with each other to transfer rotational motion to the support member 319. Further, the effector 301 performs pitching motion according to rotation of the support member 319.

Further, the gear part may be formed of at least one selected from a group consisting of a spur gear, a helical gear, a worm gear, a rack gear, and a bevel gear.

Hereinafter, configurations and operations of a forceps part of an end effector used in an SOBW type surgical operation apparatus according to preferred embodiments of the present invention will be described.

Figure 10:
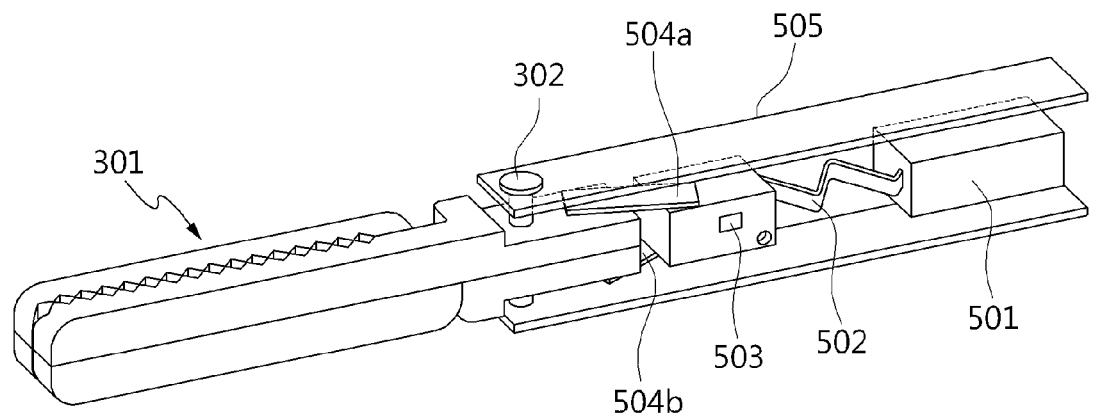
FIG. 10 is an enlarged view of configurations of a forceps part in an end effector used in an SOBW type surgical operation apparatus according to another preferred embodiment of the present invention.

FIG. 10 is an enlarged view of configurations of a forceps part in an end effector used in an SOBW type surgical operation apparatus according to another preferred embodiment of the present invention.

Referring to FIG. 10, a gripping operator of the SOBW type surgical operation apparatus according to another preferred embodiment of the present invention is configured to include a power source transfer part 501, a piezoelectric material 502, a linear motion transfer member 503, a first connection member 504a, a second connection member 504b, and a support member 505.

The power source transfer part 501 transfers the electrical energy transferred through the body part and the extension part to the piezoelectric material 502.

The piezoelectric material 502 receives the electrical energy to perform a mechanical contraction or relaxation operation. The piezoelectric material 502 is made of at least one of ceramics with perovskite structures, ceramics with tungsten-bronze structures, and a polyvinylidene fluoride (PVDF) polymer.

The piezoelectric material refers to a material which induces dielectric polarization when it is mechanically deformed or, inversely, causes mechanical deformation when an electric field is applied thereto. Piezoelectric materials are classified into a natural material and an artificial material. Quartz, berlinite (AlPO4), topaz, tourmaline, etc., are examples of the natural material. The artificial material is formed by synthesizing material which is more inexpensive than natural material. The artificial material has superior piezoelectric characteristics. Artificial piezoelectric ceramics with perovskite or tungsten-bronze structures, an artificial piezoelectric crystal and polyvinylidene fluoride (PVDF) which is a polymer are representative examples of the artificial material.

The PVDF exhibits piezoelectricity several times greater than quartz. Unlike ceramics where the crystal structure of the material creates the piezoelectric effect, in polymers the long-chain molecules attract and repel each other when an electric field is applied. In the preferred embodiment of the present invention, such PVDF layers are placed on top of one another and used to control the gripping operation of the forceps of the end effector.

In the preferred embodiment of the present invention, in lieu of the piezoelectric material, a pneumatic linear actuator, a pneumatic tube, a pneumatic cylinder, an electromagnet, etc., may he used.

The linear motion transfer member 503 is formed at one end of the piezoelectric material 502. In addition, the linear motion transfer member 503 induces the gripping operation of the effector 301 while linear moving according to the mechanical contraction or relaxation operation of the piezoelectric material 502. That is, the linear motion transfer member 503 includes the first connection member 504a connected to the first leg of the effector 301 and the second connection member 504b connected to the second leg of the effector 301, and the first and second connection members 504a and 504b transfer force to the first and second legs of the effectors 301 in different directions according to the linear motion of the linear motion transfer member 503.

The support member 505 may he configured to support the support pin 302 of the effector 301.

Figure 11:
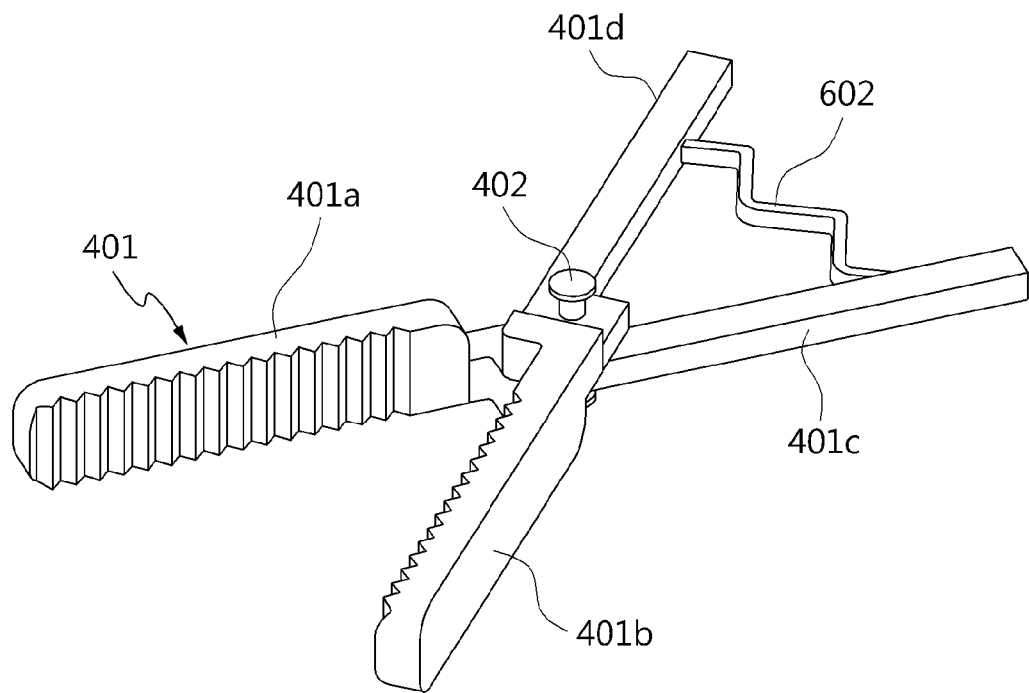
FIG. 11 is an enlarged view of configurations of a forceps part in an end effector used in an SOBW type surgical operation apparatus according to still another preferred embodiment of the present invention.

FIG. 11 is an enlarged view of configurations of a forceps part in an end effector used in an SOBW type surgical operation apparatus according to still another preferred embodiment of the present invention.

Referring to FIG. 11, the SOBW type surgical operation apparatus according to still another preferred embodiment of the present invention is configured to include a power source transfer part (not illustrated) and a piezoelectric material 602. In addition, an effector 401 includes a first leg part and a second leg part. Further, the first and second leg parts may perform a grapping operation based on a support pin 402.

Here, the first leg part is configured to include a first forceps part 401a and a first sub leg part 401c extended from the first forceps part 401a. The second leg part is configured to include a second forceps part 401b and a second sub leg part 401d extended from the second forceps part 401b.

In addition, the piezoelectric material 602 is coupled to one end of the first sub leg part 401c and one end of the second sub leg part 401d. Further, the piezoelectric material 602 may perform a mechanical contraction or relaxation operation through received electrical energy to implement the grapping operation of the effector 401.

To perform the gripping, pitching, rolling, or yawing motion of the end effector, the present invention introduces a new concept, named surgical operation by wire (SOBW), to the surgical operation apparatus 100 such as a surgical operation robot. For this, the driving part is disposed in the distal end of the extension part 200 to which the surgical operation end effector is connected, such that a mechanical cable may be removed or the number of mechanical cables may be minimized. In other words, in the conventional technique, driving parts such as electrical motors, the number of which corresponds to the number of degrees of freedom of motion of the end effector are disposed in the body part of the surgical operation apparatus, and cables, the number of which corresponds to the number of degrees of freedom of motion of the end effector, connect the driving parts to the end effector. However, the present invention does not require any cable. If as shown in the description of the conventional technique, the distance between the driving part and the end effector is comparatively long, there is a problem of backlash. As the number of degrees of freedom of motion of the end effector is increased, the structure of the apparatus becomes complicated to prevent the cables from being entangled. Given this, in the present invention, the driving part which has been disposed in the body part in the conventional technique is disposed in the distal end of the extension part, thus reducing the distance between the driving part and the end effector. In lieu of cables, a gear is used to transfer driving force from the driving part to the end effector, thereby fundamentally avoiding a problem related to the tension of the cables. This is an application of technology of reducing the size of a power source such as an electrical motor. As a result, the operation of the end effector may be more precisely and accurately controlled. The electrical motor, or the like, is connected to the body part through an electrical wire, whereby a surgical operation is controlled by the electrical wire through which electrical signals are transmitted and received rather than by the cables that have tension. In this sense, a concept that is called surgical operation by wire (SOBW) is introduced.

In the preferred embodiment of the present invention, the adjustment of the joints of the active part of the extension part 200 that extends from the body part of the surgical operation apparatus 100 and controlling gripping, pitching, rolling or yawing motion of the end effector may be performed in such a way that a doctor manipulates a controller attached or connected to the body part of the surgical operation apparatus 100 rather than using cables. That is, when the doctor manipulates the controller, variation in the controller is converted into an electrical signal, and it is transmitted to the driving unit that is disposed adjacent to the end effector. The driving unit that receives the signal generates driving force and transmits it to the end effector through a gear or the like. In this way, an SOBW type surgical operation apparatus technology can be implemented.

According to the preferred embodiment of the present invention, it is possible to prevent a mechanical cable from being extended and cut and prevent a backlash phenomenon by minimizing configurations of the mechanical cable.

In addition, the present invention has a configuration in which the mechanical cable is replaced by the gear, thereby making it possible to improve work precision of the end effector. Further, the prevent invention may reduce diameters of the connection part and the end effector. Therefore, the present invention minimizes an incision entering the abdominal cavity to decrease bleeding of a patient and ultimately minimize a side effect due to a surgical operation, thereby making it possible to maximize an advantage of minimally invasive surgery.

Furthermore, the present invention allows driving force to directly act on the effector rather than using cable tension and frictional force, thereby making it possible to improve work precision.

In the SOBW type surgical operation apparatus according to the preferred embodiment of the present invention as described above, the configuration and the method of the above-mentioned preferred embodiments are not restrictively applied. That is, all or some of the respective preferred embodiments may be selectively combined with each other so that they may be variously modified.

What is claimed is:

1. A surgical operation by wire (SOBW) type surgical operation apparatus, comprising:
   a body part;
   an extension part having one end connected to the body part; and
   an end effector formed at the other end of the extension part, and for receiving electrical energy transferred through the body part and the extension part and converting the electrical energy into mechanical energy,
   the end effector includes a pitching operator;
   wherein the pitching operator comprises:
   a pitching motor part;
   a first gear connected to the pitching motor part;
   a second gear formed perpendicularly to the first gear and supported to a second gear support bar; and
   a third gear connected to the second gear and supported to a third gear support bar;
   wherein the end effector comprises:
   an effector for accessing a surgical operation target site to perform a surgical operation work; and
   a gripping operator receiving the electrical energy transferred from the body part and the extension part to induce a gripping operation of the effector,
   wherein the gripping operator comprises:
   a gripping motor part converting the electrical energy into rotational motion; and
   a gripping extension part converting the rotational motion of the gripping motor part into linear motion to induce the gripping operation of the effector,
   a sub extension part which is pivot-coupled to an end of the gripping extension part through a pivot coupling part;
   a support member which is formed to support the effector; and
   a groove part which is formed in a portion of an inner side of the support member to accommodate motion of the sub extension part inward.

2. The SOBW type surgical operation apparatus as set forth in claim 1, wherein the effector is formed of forceps comprising first and second legs, and
   the gripping operator further comprises a linear motion transfer member formed at one end of the gripping extension part and transferring force to each of the first and second legs in different directions.

3. The SOBW type surgical operation apparatus as set forth in claim 2, wherein the gripping operator further comprises:
   a first connection member formed at one side of the linear motion transfer member and coupled to one end of the first leg; and
   a second connection member formed at the other side of the linear motion transfer member and coupled to one end of the second leg, and
   the first and second connection members transfer force to the first and second legs in different directions, respectively, according to linear motion of the linear motion transfer member.

4. The SOBW type surgical operation apparatus as set forth in claim 1, wherein:
   the pitching motor part converts the electrical energy into rotational motion; and
   the first, second, and third gears induce the pitching operation of the effector through the rotational motion of the pitching motor part.

5. The SOBW type surgical operation apparatus as set forth in claim 4, wherein the first, second, and third gears are part is formed of at least one selected from a group consisting of a spur gear, a helical gear, a worm gear, a rack gear, and a bevel gear.

6. The SOBW type surgical operation apparatus as set forth in claim 1, wherein the effector is any one of forceps, scissors, a needle driver, a clip applier, a probe grasper, and a retractor.

* * * * *